United States Patent
Sugio et al.

(10) Patent No.: US 8,357,101 B2
(45) Date of Patent: Jan. 22, 2013

(54) ELECTRO-OCULOGRAPHY APPARATUS, IMAGING APPARATUS, ELECTRO-OCULOGRAPHY METHOD, PROGRAM, AND INTEGRATED CIRCUIT

(75) Inventors: Toshiyasu Sugio, Osaka (JP); Daisuke Sato, Osaka (JP)

(73) Assignee: Panasonic Corporation, Osaka (JP)

( * ) Notice: Subject to any disclaimer, the term of this patent is extended or adjusted under 35 U.S.C. 154(b) by 688 days.

(21) Appl. No.: 12/468,508

(22) Filed: May 19, 2009

(65) Prior Publication Data

US 2009/0292223 A1    Nov. 26, 2009

(30) Foreign Application Priority Data

May 20, 2008    (JP) .................................. 2008-131506

(51) Int. Cl.
*A61B 13/00* (2006.01)
*A61B 5/04* (2006.01)
(52) U.S. Cl. ........................................ 600/558; 600/546
(58) Field of Classification Search .................. 600/558, 600/546, 544; 351/200, 205–210
See application file for complete search history.

(56) References Cited

U.S. PATENT DOCUMENTS 4,653,001 A * 3/1987 Semenov et al. ............. 600/558
6,091,334 A * 7/2000 Galiana et al. ................ 600/558

FOREIGN PATENT DOCUMENTS

JP    11-85384    3/1999

OTHER PUBLICATIONS

Fitch, JP. "Software and VLSI Alogrithms for Generalized Ranked Order Filtering." IEEE Transactions on Circuits and Systems. vol. Cas-34, No. 5, pp. 553-559. May 1987.*
Hiroyuki Manabe et al., "Headphone shaped eye-gaze interface", [http://www.interaction-psj.org/archives/paper2006/pdf2006/interactive/paper0149.pdf], NTT DoCoMo Multimedia Laboratories, Interaction 2006, Mar. 2, 2006, [http://www.interaction-ipsj.org/2006/prg_int2006.html], (with relevant English document, Full-time Wearable Headphone-Type Gaze Detector, CHI 2006 Work-in-Progress, Apr. 22-27, 2006, Montreal, Quebec, Canada.

* cited by examiner

*Primary Examiner* — Jeffrey G Hoekstra
*Assistant Examiner* — Megan Leedy
(74) *Attorney, Agent, or Firm* — Wenderoth, Lind & Ponack, L.L.P.

(57) ABSTRACT

An electro-oculography apparatus 100 includes an eye potential measuring unit measuring an eye potential generated by an eye movement and outputting an eye potential original signal, and includes a minimum filtering unit 121 or a maximum filtering unit 123 each outputting a first eye potential signal by applying one of a maximum value filtering and a minimum value filtering to the eye potential original signal. The electro-oculography apparatus 100 also includes a maximum filtering unit 122 or a minimum filtering unit 124 each outputting a second eye potential signal by applying the other of the maximum value filtering and the minimum value filtering to the first eye potential signal.

10 Claims, 16 Drawing Sheets

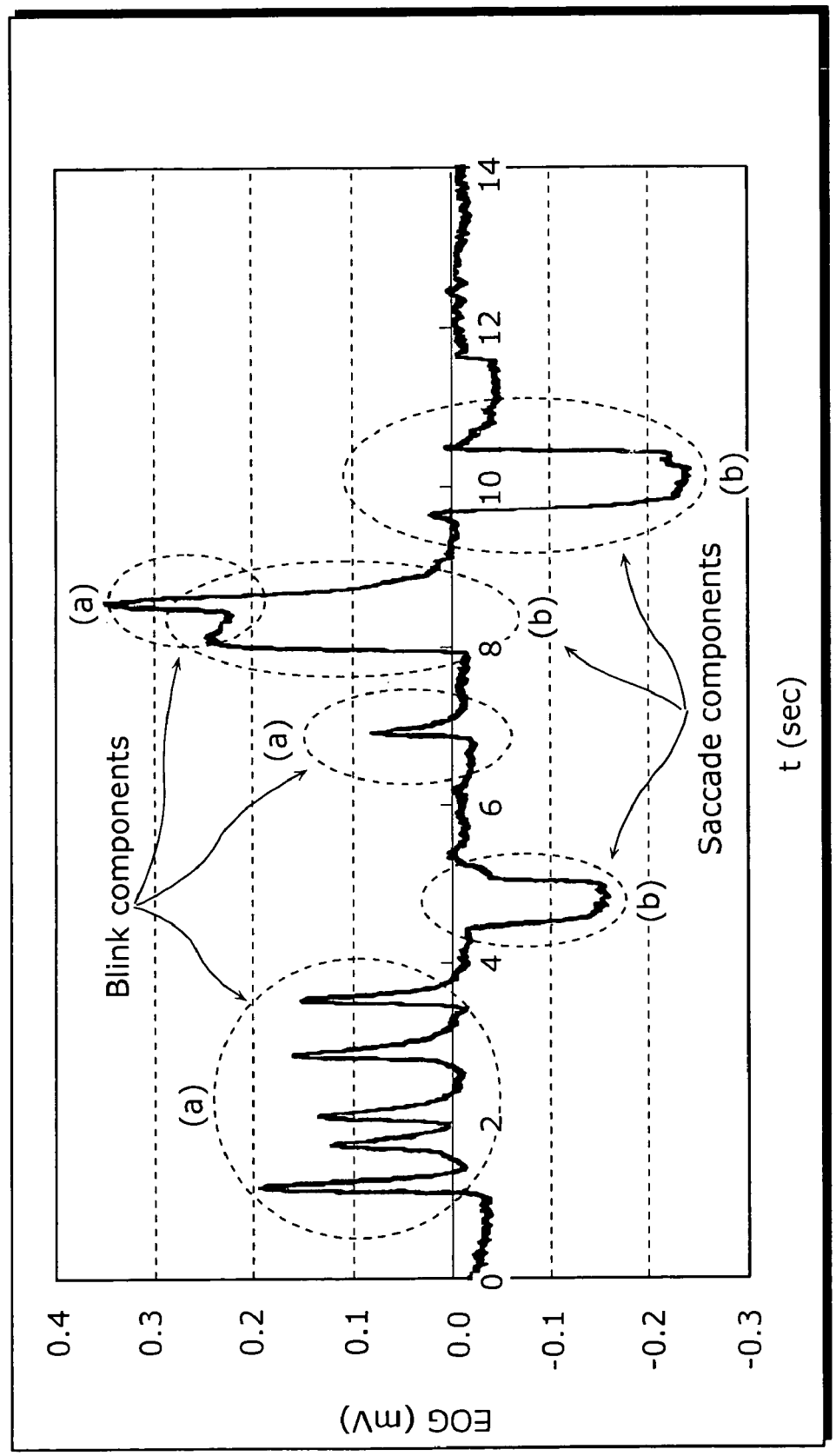

ELECTRO-OCULOGRAPHY APPARATUS, IMAGING APPARATUS, ELECTRO-OCULOGRAPHY METHOD, PROGRAM, AND INTEGRATED CIRCUIT

BACKGROUND OF THE INVENTION (1) Field of the Invention

The present invention relates to an electro-oculography apparatus that removes or detects a signal generated by an eye blink and further detects a saccade signal in an eye potential signal of a user with ease and high accuracy.

(2) Description of the Related Art

Methods for detecting an eye movement includes: an electro-oculography (EOG) that utilizes a potential generated between a cornea and a retina; a corneal reflex method that detects a movement of a virtual image generated on a cornea by irradiating a spotlight on an eyeball; a strong-reflection method that uses a difference in reflectance between the cornea and the retina; a method using contact lenses; and so on.

Here, the EOG is a method for detecting an eye movement that utilizes the fact that a human cornea is charged positively with respect to the retina. More specifically, electrodes are placed near a human eyeball and a change in a potential measured by the electrodes is used to detect the eye movement.

FIG. 14A and FIG. 14B show examples of the method for detecting an eye movement which employs the EOG. FIG. 14A shows an example of the case where electrodes A and B are placed to the outside and the inside of the right eye of a user, the same distance away from the center of the eyeball, in which the outer electrode is A and the inner electrode is B. Assuming the eye potential occurring on the electrode A is Va and the eye potential occurring on the electrode B is Vb, Va and Vb are equal when the eyeball of the user is positioned in the center as in FIG. 14A, and the eye potential $V_{a-b}$ measured is 0V.

On the other hand, when the user looks to the right as in FIG. 14B, the electrode A becomes closer to the cornea of the right eye, and thus Va becomes greater than Vb and the measured eye potential $V_{a-b}$ indicates a positive value. Conversely, when the user looks to the left, Va becomes smaller than Vb and the measured eye potential $V_{a-b}$ indicates a negative value. In other words, when the measured eye potential $V_{a-b}$ shows a positive value, it is indicated that the user has moved his or her eye to the right, and when the measured eye potential $V_{a-b}$ shows a negative value, it is indicated that the user has moved the eye to the left. In the EOG method, such changes in the measured eye potential $V_{a-b}$ as described above are utilized, so that an eye movement of a user is detected.

When detecting an eye movement by utilizing a change in an eye potential as in the EOG and the like, there is a problem of an effect of a signal generated by a blink of a user (hereinafter referred to as "blink signal").

In some cases, the blink signal is generated invariably in the positive direction, or invariably in the negative direction, depending on the method for measuring the eye potential.

FIG. 15A to FIG. 15D show examples of patterns of placing the electrodes and the methods for measuring the blink signal. According to the placement pattern of FIG. 15A, the electrodes A and B are placed above and below an eye, respectively, and a difference potential Va-Vb is obtained, where Va is the eye potential measured by the electrode A placed above the eye and Vb is the eye potential measured by the electrode B placed below the eye. In this case, the blink signal is generated invariably in the positive direction. This is because, when a human blinks, the eyeball always moves upward.

According to the placement pattern of FIG. 15B, the electrode A is placed above the eye and the other electrode is placed on the earth or a place less subject to the eye potential, so that the eye potential Va of the electrode A is measured. In this case also, the blink signal is generated invariably in the positive direction (at a value larger than a reference value).

Likewise, according to the placement pattern of FIG. 15C, the electrodes A and B are placed above and below the eye, respectively, and a difference potential Vb-Va is obtained, where Vb is the eye potential measured by the electrode B placed below the eye and Va is the eye potential measured by the electrode A placed above the eye. In this case, the blink signal is generated invariably in the negative direction. According to the placement pattern of FIG. 15D, the electrode B is placed below the eye and the other electrode is placed on the earth or a place less subject to the eye potential, so that the eye potential Vb of the electrode B is measured. In this case also, the blink signal is generated invariably in the negative direction.

When the user blinks during the measurement of the eye potential according to the placement patterns as shown in FIG. 15A and FIG. 15B, a potential is generated steeply in the positive direction (this is the "blink signal") as shown by regions (a) in FIG. 16. When the signal is treated directly as an eye-gaze movement, a gaze-point changes rapidly and a gaze-path cannot be tracked accurately.

Here, there is a technique disclosed by Japanese Unexamined Patent Application Publication No. 11-85384 (Patent Reference 1) as a method to reduce an effect of the blink signal (a component of a signal generated by a blink) and the like from eye potential original signal.

The technique disclosed by Patent Reference 1 aims to detect an eye potential of a user and input a gaze-position (cursor) in real time. At this time, a delay element is introduced into a fluctuation waveform of the eye potential, so that a temporal change in the gaze-position (cursor) is smoothed and a rapid change in the gaze-position caused by a blink is reduced.

Further, there is a technique disclosed by "Full-time Wearable Headphone-Type Gaze Detector", Interaction 2006, pages 23 to 24, 2006 (Non-Patent Reference 1), Hiroyuki Manabe, Masaaki Fukumoto, as a technique reducing an effect of the blink signal.

According to the technique disclosed in the Non-Patent reference 1, a total of 8 electrodes are placed on the right and left of a headphone. A median filter is applied at 0.4 second intervals as to changes in the eye potential obtained from the 8 electrodes, thereby removing a change caused by a blink signal that is shorter than the above-described time interval.

However, as shown in the Patent Reference 1, merely temporally smoothing the eye potential original signal causes an adverse effect that the smoothing is performed even on a saccade waveform indicating a component change in a saccade (a rapid movement of a human eye from one gaze-point to another gaze-point (saccadic movement)) that is important in tracking a gaze-path.

Here, a saccade (saccadic eye movement) is an eye movement that occurs due to capturing an object projected on a peripheral retina where resolution is low, at a central fovea of retina where resolution is high. It is known that the speed is significantly high, at 100 to 500 (°/sec). In FIG. 16, the saccade signal is shown in portions indicated as regions (b), in which a potential changes rapidly, retains the level for a fixed amount of time (fixation), and then returns to the original potential level. This is an example of the case where an eyeball is moved in saccade from a target A to a target B, and then moved again in saccade from the target B to the target B.

In general, a human obtains information on surroundings by repeating fixation for approximately 0.3 seconds and saccade for several dozen milliseconds.

When a median filter is applied to the eye potential original signal as shown in the Non-Patent reference 1, although blink signal that has been generated singly can be removed as shown in FIG. 17, the effects of blink signals that have been generated continuously for at least a predetermined amount of time cannot be completely removed. In addition, an adverse effect that a part of the saccade waveform breaks is caused.

Therefore, the above-described references have not made it clear what smoothing filter should be applied how long and in what order is optimum, in consideration of removal of blink signal and retaining saccade signal.

SUMMARY OF THE INVENTION

The present invention has been conceived in order to present a solution to the above-stated problems and aims to provide an electro-oculography apparatus that removes or detects a blink signal and further detects a saccade signal in eye potential signal of a user with ease and high accuracy.

The electro-oculography apparatus according to an aspect of the present invention measures an eye potential of a user. More specifically, the electro-oculography apparatus measures an eye potential, and includes: an eye potential measuring unit configured to measure the eye potential generated by an eye movement and to output an eye potential original signal; a first filtering unit configured to output a first eye potential signal by applying one of a maximum value filtering and a minimum value filtering to the eye potential original signal; and a second filtering unit configured to output a second eye potential signal by applying the other of the maximum value filtering and the minimum value filtering to the first eye potential signal. With the above-described configuration, it is possible to selectively remove only a blink signal without breaking a saccade waveform.

Further, the electro-oculography apparatus may include a filtering detail determination unit configured to determine processing to be performed by the first and second filtering units based on a blink signal included in the eye potential original signal, the blink signal being generated when the user blinks. This makes it possible to remove the blink signal properly even when the position of the eye potential measuring unit (electrode) changes.

As an embodiment, the filtering detail determination unit may be configured to cause: the first filtering unit to perform the minimum value filtering; and the second filtering unit to perform the maximum value filtering, when the blink signal has a positive potential.

Further, a unit processing period of the minimum value filtering may be equal to a unit processing period of the maximum value filtering. This makes it possible to restore the saccade waveform to original state.

Further, the electro-oculography apparatus may include a subtraction unit configured to subtract the second eye potential signal from the eye potential original signal. This makes it possible to extract only the blink signal selectively from the eye potential original signal.

Further the electro-oculography may include a subtraction unit configured to subtract the first eye potential signal from the second eye potential signal. This makes it possible to extract only the saccade signal selectively from the eye potential original signal.

Further, a unit processing period of the maximum value filtering may be greater than a unit processing period of the minimum value filtering. This makes it possible to obtain the saccade signal including the time when the saccade occurred.

Further, the unit processing period of each of the maximum value filtering and the minimum value filtering may be equal to or greater than a blink duration of the user and less than a fixation time. This makes it possible to remove only the blink signal properly without breaking the saccade waveform.

As another embodiment, the filtering detail determination unit may be configured to cause: the first filtering unit to perform the maximum value filtering; and the second filtering unit to perform the minimum value filtering, when the blink signal has a negative potential.

An imaging apparatus according to an aspect of the present invention takes an image along a gaze direction of a user. More specifically, the imaging apparatus includes: an imaging unit; an electro-oculography apparatus described above; a calibration unit configured to detect the gaze direction of the user, using an output signal of the electro-oculography apparatus; and an image control unit configured to cause the imaging unit to image the gaze direction detected by the calibration unit. With the above-described configuration, it is possible to detect the gaze-path while eliminating an effect of the blink signal. Therefore, it is possible to properly take an image along the gaze direction of the user.

An electro-oculography method according to an aspect of the present invention measures an eye potential of a user. More specifically, the electro-oculography method includes: measuring an eye potential generated by an eye movement and outputting an eye potential original signal; outputting a first eye potential signal by applying one of a maximum value filtering and a minimum value filtering to the eye potential original signal; and outputting a second eye potential signal by applying the other of the maximum value filtering and the minimum value filtering to the first eye potential signal.

A program according to an aspect of the present invention causes a computer to measure an eye potential of a user, the computer being connected to an eye potential measuring unit that measures an eye potential generated by an eye movement and outputs an eye potential original signal. More specifically the program includes: outputting a first eye potential signal by applying one of a maximum value filtering and a minimum value filtering to the eye potential original signal; and outputting a second eye potential signal by applying the other of the maximum value filtering and the minimum value filtering to the first eye potential signal.

An integrated circuit according to an aspect of the present invention measures an eye potential of a user when connected to an eye potential measuring unit that measures an eye potential generated by an eye movement and outputs an eye potential original signal. More specifically, the integrated circuit includes: a first filtering unit configured to output a first eye potential signal by applying one of a maximum value filtering and a minimum value filtering to the eye potential original signal; and a second filtering unit configured to output a second eye potential signal by applying the other of the maximum value filtering and the minimum value filtering to the first eye potential signal.

It should be noted that the present invention can be embodied not only as an electro-oculography apparatus, but also as an integrated circuit that implements the function of the electro-oculography apparatus and as a program which, when loaded into a computer, allows a computer to execute the function. Further, such a program may be distributed, of course, via recording medium such as a CD-ROM and communication medium such as the Internet.

According to the present invention, it is possible to obtain an electro-oculography apparatus that is capable of removing only the blink signal selectively from the eye potential original signal by applying a maximum value filtering and a minimum value filtering.

Further Information about Technical Background to this Application

The disclosure of Japanese Patent Application No. 2008-131506 filed on May 20, 2008 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 16 is a diagram that shows an example of an eye potential signal that includes a blink signal.

DESCRIPTION OF THE PREFERRED EMBODIMENTS

Embodiments according to the present invention will be described below with reference to the drawings. It is to be noted that each embodiment described below may be combined with other embodiment in an arbitrary combination unless an advantageous effect of the present invention is diminished due to the combination.

First Embodiment

Figure 1:
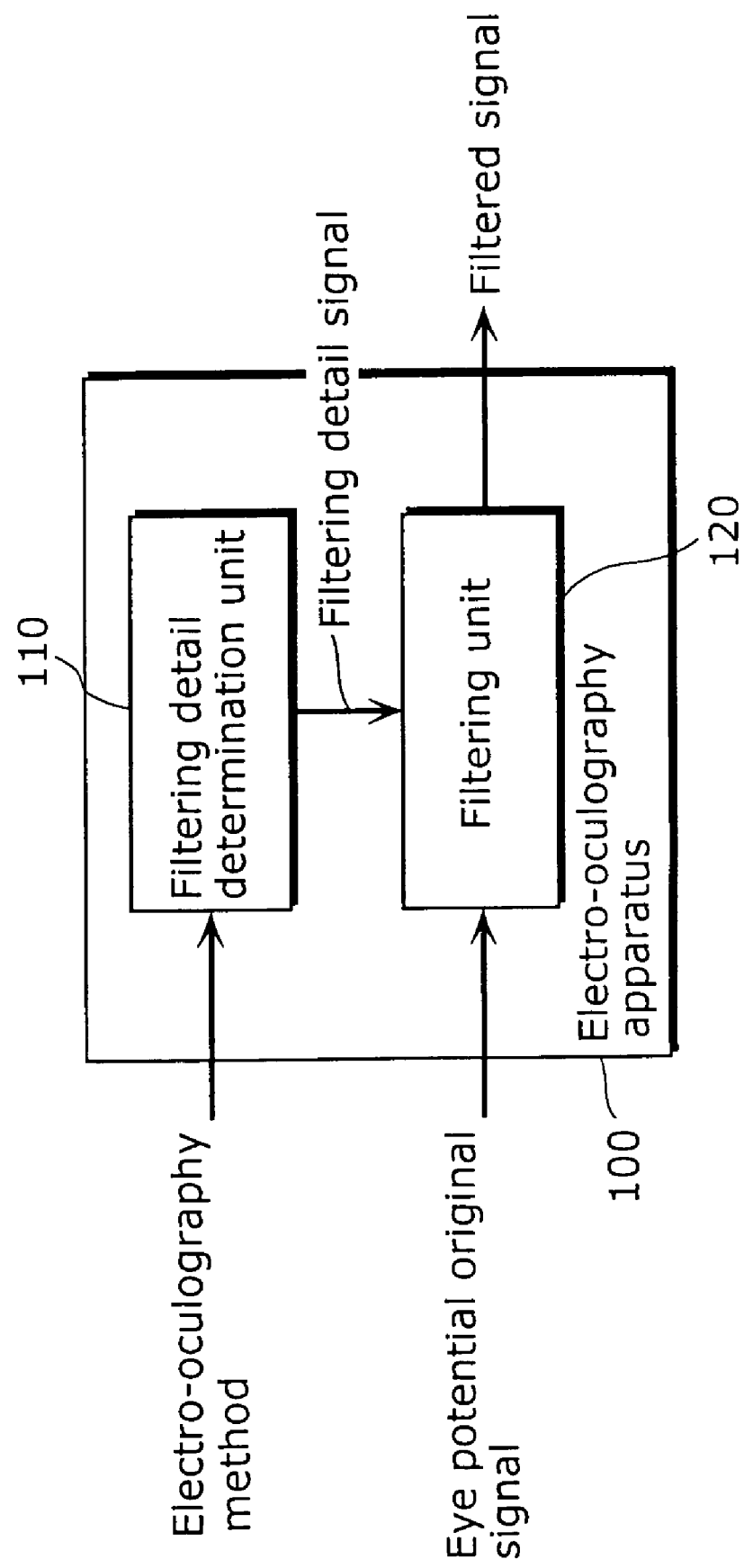
FIG. 1 is a block diagram of an electro-oculography apparatus according to a first embodiment.

FIG. 1 is a block diagram that shows a configuration of an electro-oculography apparatus 100 according to first embodiment of the present invention.

The electro-oculography apparatus 100 includes: an eye potential measuring unit (illustration omitted) placed around a user's eye to measure an eye potential and output an eye potential original signal; a filtering detail determination unit 110 that determines a detail of filtering using a signal indicating how to measure the eye potential (in the diagram: eye potential measuring method); and a filtering unit 120 that applies filtering to the eye potential original signal according to a filtering detail signal.

First, the method of measuring the eye potential may be specified in advance by an experimenter or a user, or may be estimated based on a tendency of change in the eye potential original signal.

Figure 14B:
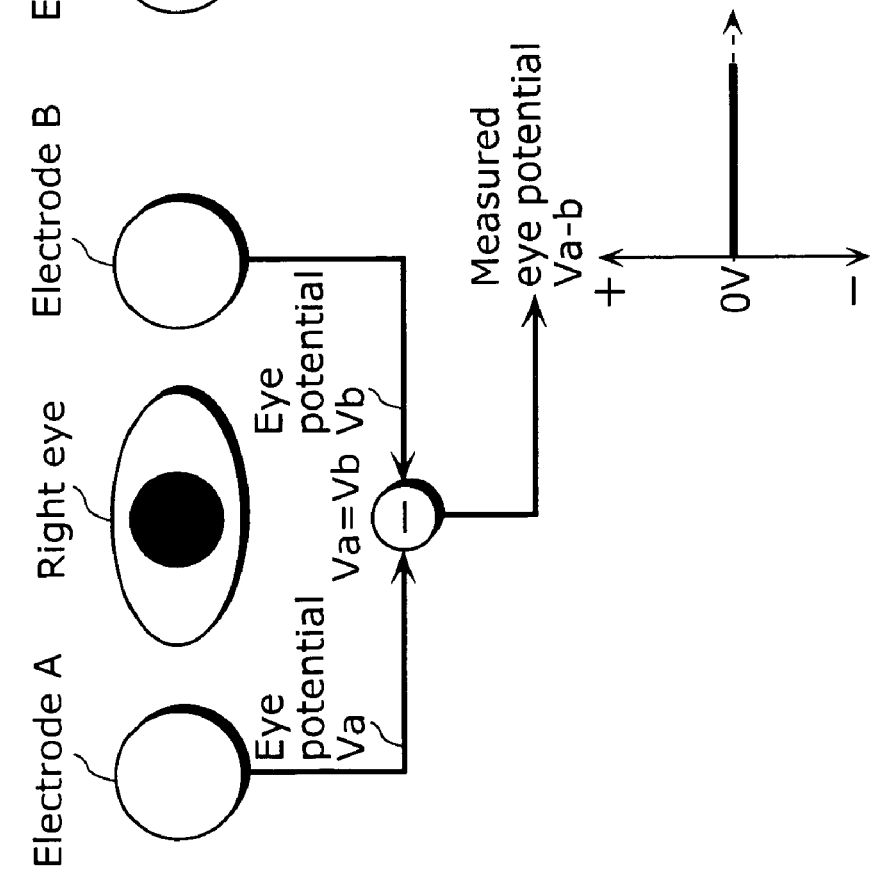
FIG. 14B is a diagram which explains the EOG and shows a user's eyeball facing right.
Figure 14A:
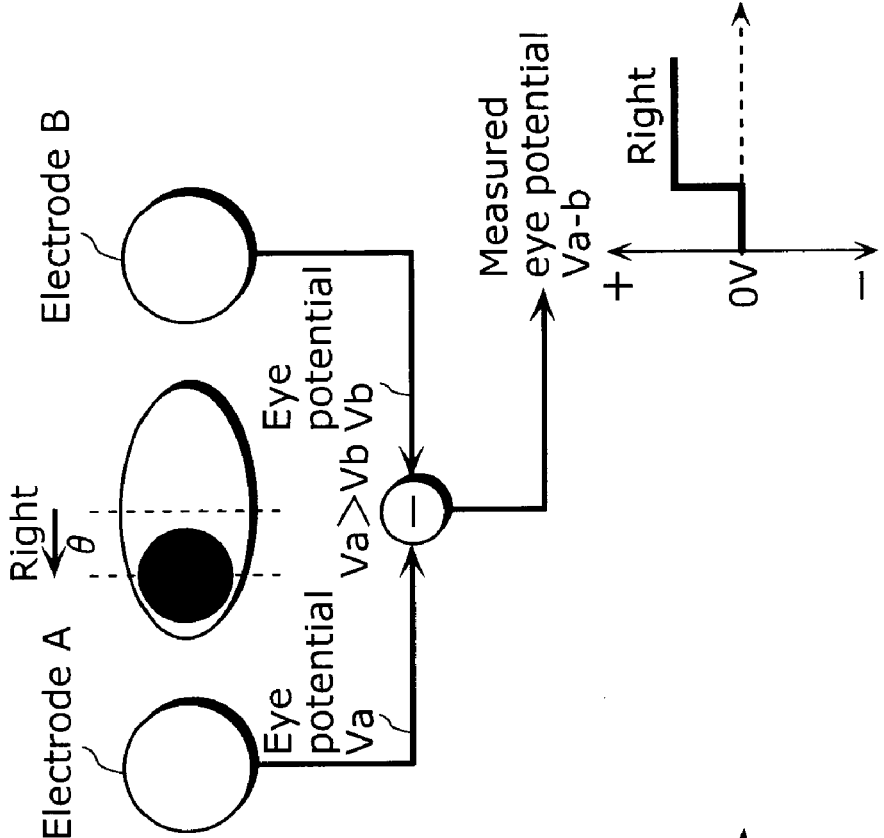
FIG. 14A is a diagram which explains an EOG and shows a user's eyeball facing front.
Figure 15B:
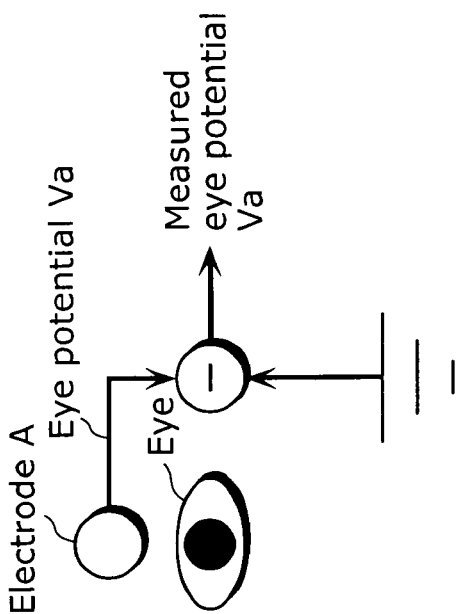
FIG. 15B is a diagram that shows another example of a pattern of attaching electrodes.
Figure 15D:
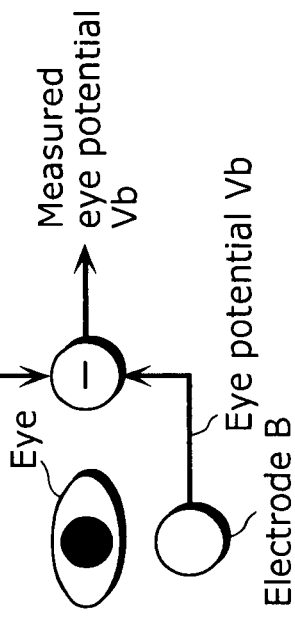
FIG. 15D is a diagram that shows another example of a pattern of attaching electrodes.
Figure 15A:
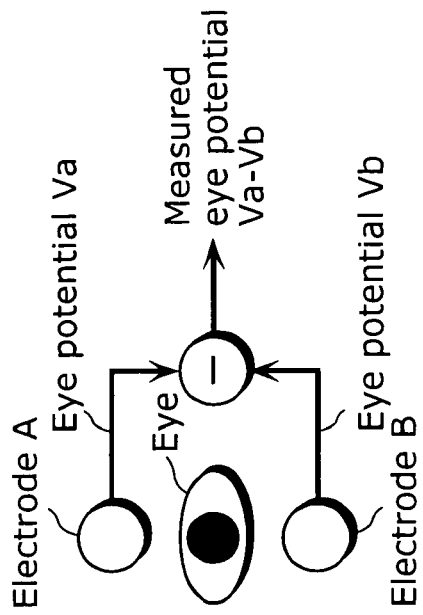
FIG. 15A is a diagram that shows an example of a pattern of attaching electrodes.

More specifically, the user may specify a measuring method that places electrodes A and B on the right and left, respectively, of an eyeball as shown in FIGS. 14A and 14B, or it may be estimated that the placement pattern as shown in FIG. 15A and FIG. 15B is employed for the measuring method in the case where a signal is generated upward in the eye potential original signal whenever the user blinks.

Figure 2:
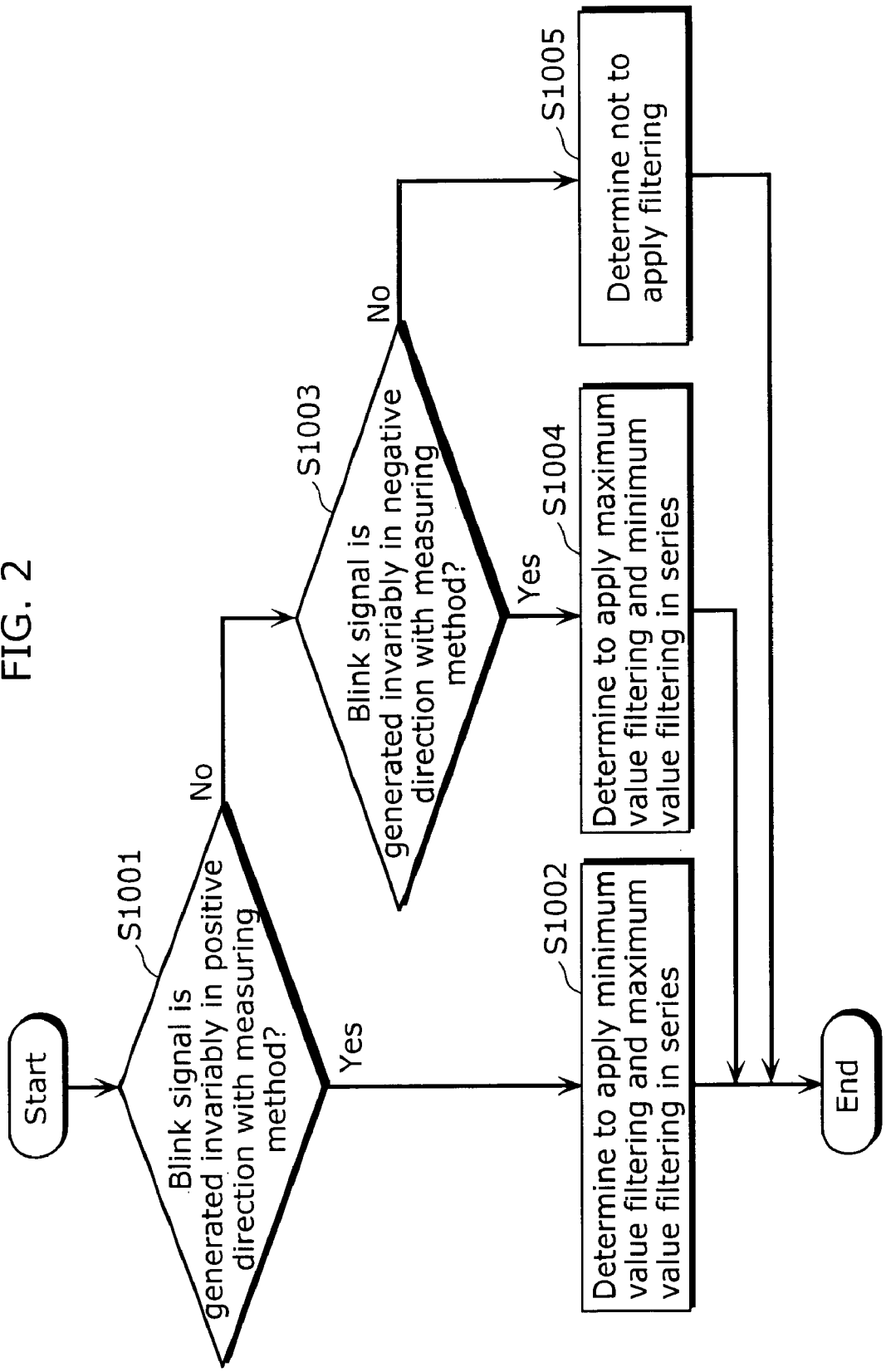
FIG. 2 is a flow chart that shows operations of a filtering detail determination unit.

FIG. 2 is a flow chart that shows operations of the filtering detail determination unit 110. The filtering detail determination unit 110 determines an order of applying a filter (described later) in the filtering unit 120 to first remove an effect of a blink. Further, although not shown, the number of necessary taps (time) is determined depending on the difference of electro-oculography methods. Furthermore, whether or not a filter is to be applied changes depending on whether the electrodes placed in advance are placed in a horizontal direction or in a vertical direction.

More specifically, it is determined whether or not a blink signal is generated invariably in the positive direction with the measuring method as in the placement pattern of FIG. 15A and FIG. 15B (Step S1001). When the blink signal indicates invariably a positive potential (Yes in Step S1001), a filtering detail is determined so that minimum value filtering and maximum value filtering are applied in this order (Step S1002).

Figure 15C:
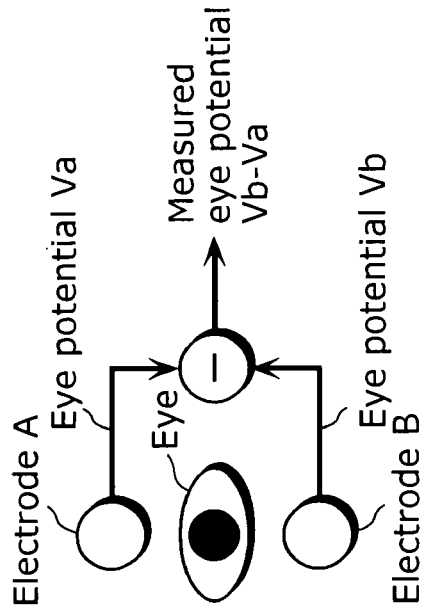
FIG. 15C is a diagram that shows another example of a pattern of attaching electrodes.
Figure 17:
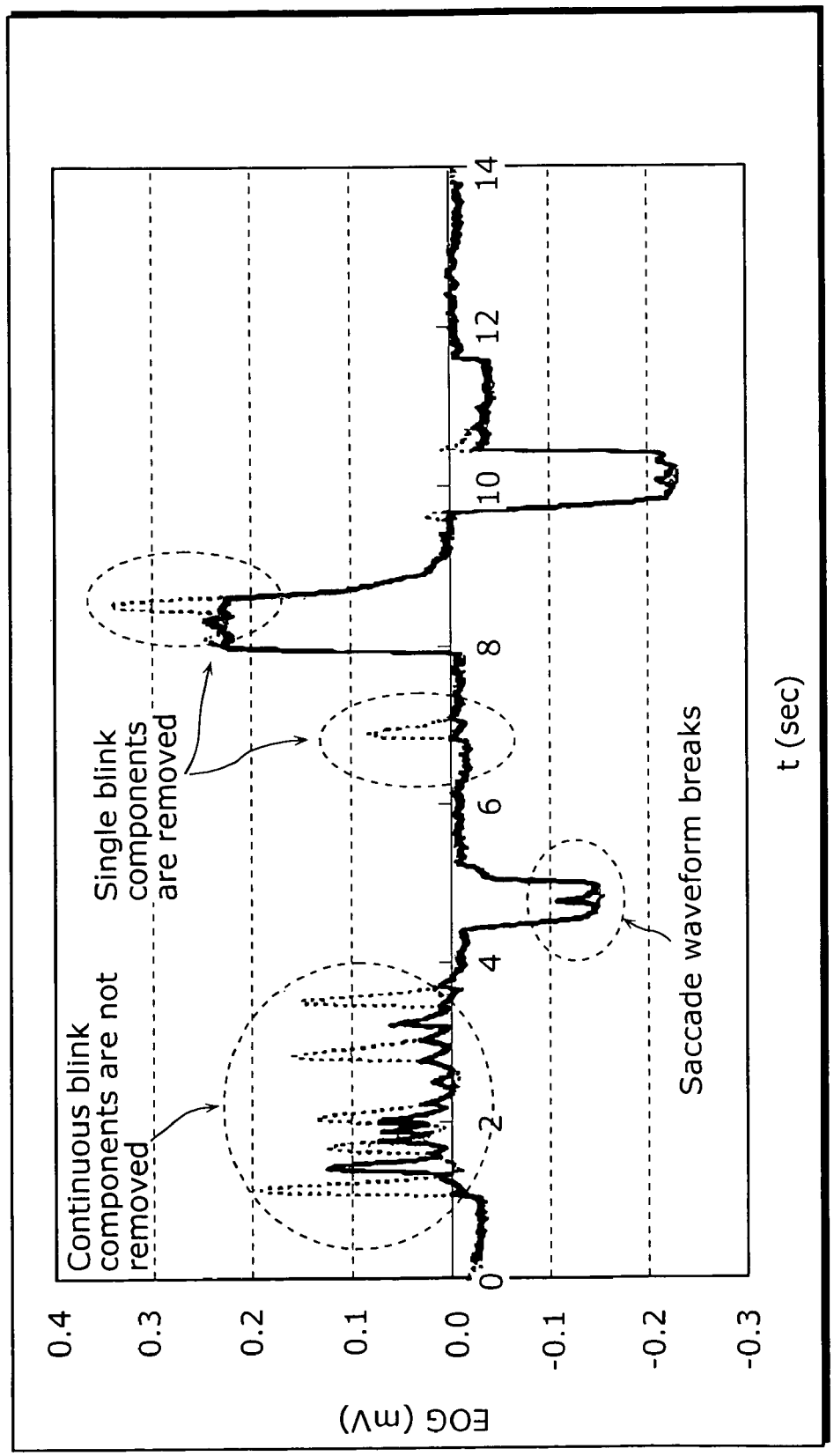
FIG. 17 is a diagram that shows an eye potential signal obtained by applying median filtering to the eye potential signal of FIG. 16.

When the blink signal does not indicate a positive potential (No in Step S1001), it is determined whether or not the blink signal is generated invariably in the negative direction with the measuring method as in the placement pattern of FIG. 15C and FIG. 15D (Step S1003). When the blink signal indicates invariably the negative potential (Yes in Step S1003), a filtering detail is determined so that maximum value filtering and minimum value filtering are applied in this order (Step S1004).

When the blink signal does not indicate a negative potential (No in Step S1003), it is determined that the measuring method is not affected by a blink, and that filtering is not to be performed for removing a blink signal (Step S1005). It is to be noted that, an example of the case where the measuring method is not affected by a blink includes: the case where electrodes A and B are placed on the right and on the left of an eye, respectively, as shown in FIG. 14A and FIG. 14B to measure the difference; and the case where electrodes A and B are placed away from an eye.

The filtering detail determination unit 110 outputs a filtering detail signal (orientation, the number of tap n, presence or absence (n=0 may also be possible to be outputted)) by including information such as an application order of the filter which has been determined in the above process, the number of tap n of the filter, and unit processing period. It is to be noted that the determination order of the above-described flow chart is an example, and any determination order may be employed.

Figure 3:
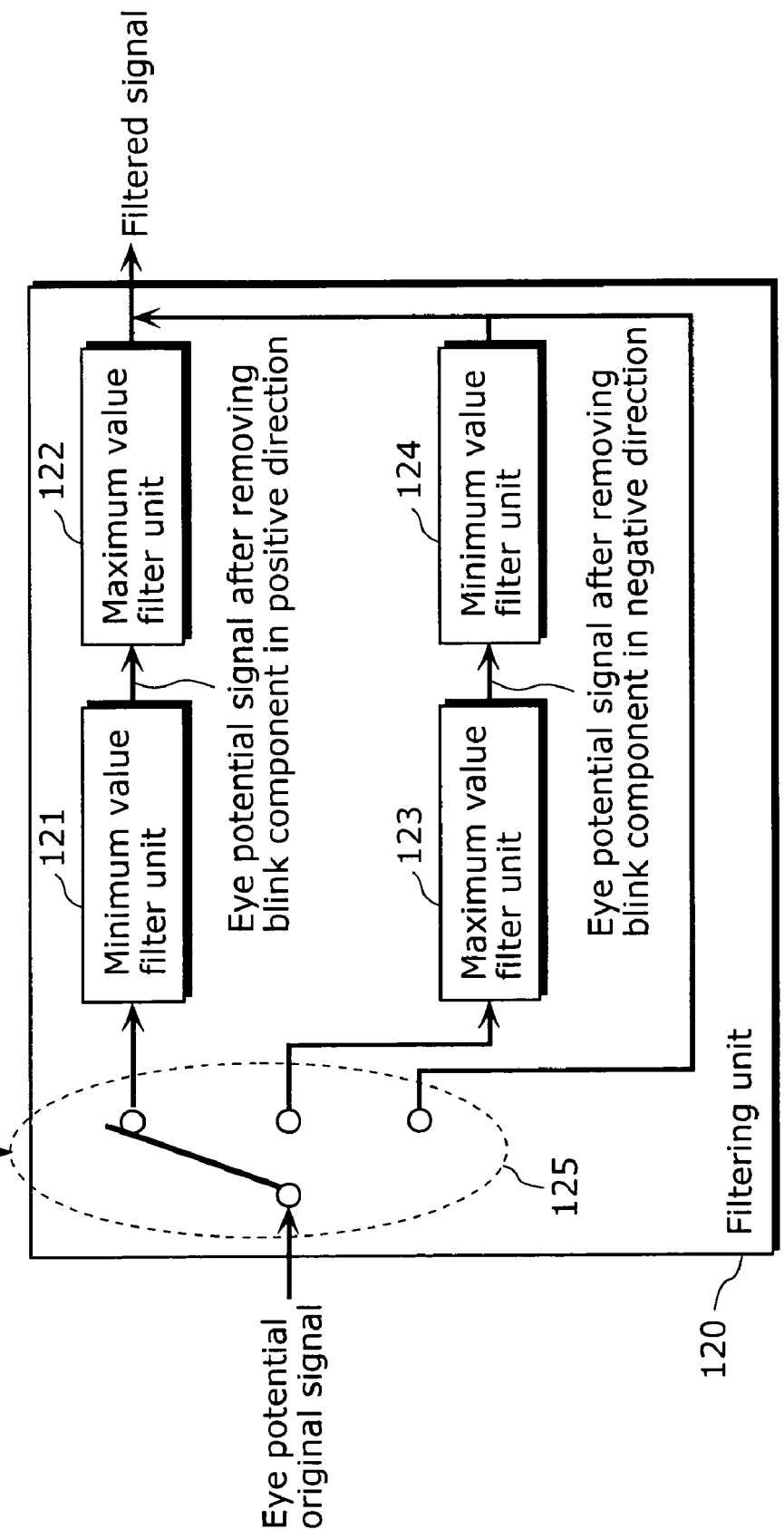
FIG. 3 is a block diagram of a filtering unit as shown in FIG. 1.

FIG. 3 is a diagram that shows a configuration of the filtering unit 120. The filtering unit 120 applies filtering on the eye potential original signal according to a signal outputted from the filtering detail determination unit 110.

A filter used in the filtering unit 120 is not a median filter, a weighting addition filter, or the like which are disclosed in the above-described prior art, but a filter for extracting the minimum value and the maximum value. Further, the minimum value filtering and the maximum value filtering are applied according to the order specified by the filtering detail signal described above so that a blink signal is to be removed first.

The filtering unit 120 includes: two minimum value filter units 121 and 124; two maximum value filter units 122 and 123; and a switch 125 that switches between a first path to a third path from an input terminal to an output terminal to connect one of the paths to which the eye potential original signal is outputted.

In the first path, a minimum value filter unit 121 (a first filtering unit) and a maximum value filter unit 122 (a second filtering unit) are connected in series, in which the minimum value filter unit 121 applies the minimum value filtering on the eye potential original signal and outputs a first eye potential signal, and the maximum value filter unit 122 applies the maximum value filtering on the first eye potential signal and outputs a second eye potential signal (filtered signal). In the second path, a maximum value filter unit 123 (a first filtering unit) and a minimum value filter unit 124 (a second filtering unit) are connected in series, in which the maximum value filter unit 123 applies the maximum value filtering on the eye potential original signal and outputs a first eye potential signal, and the minimum value filter unit 124 applies the minimum value filtering on the first eye potential signal and outputs a second eye potential signal (filtered signal). In the third path, a path that outputs the eye potential original signal without applying filtering is provided. The switch 125 switches destinations to which the eye potential original signal is outputted, according to the filtering detail determined by the filtering detail determination unit 110.

In the case where the switch 125 receives a filtering detail signal generated in Step S1002 shown in FIG. 2, the switch 125 switches a connection point to the one in the top stage shown in FIG. 3, so that the eye potential original signal is outputted to the first path. Further, in the case where the switch 125 receives a filtering detail signal generated in Step S1004 shown in FIG. 2, the switch 125 switches the connection point to the one in the middle stage shown in FIG. 3, so that the eye potential original signal is outputted to the middle path. Furthermore, in the case where the switch 125 receives a filtering detail signal generated in Step S1005 shown in FIG. 2, the switch 125 switches the connection point to the one in the bottom stage shown in FIG. 3, so that the eye potential original signal is outputted to the bottom path.

It is to be noted that, although two units are included in each of the minimum value filter unit and the maximum value filter unit, that is, the minimum value filter units 121 and 124 and the maximum value filter units 122 and 123 in the first embodiment, it may also be possible to provide a single unit for each of the minimum value filter unit and the maximum value filter unit and change an order of connection based on the filtering detail signal, and the like, to achieve the invention.

Next, operations of the minimum value filter unit 121 will be described. The minimum value filter unit 121 applies filtering described below on the eye potential original signal f (x).

$$f'(x) = \min(f'(x), f(x+i))$$

When n is an odd number, the following applies. ($-n/2 < i < n/2$)

When n is an even number, one of the followings applies. ($-n/2 \leq i < n/2$) or ($-n/2 < i \leq n/2$)

Here, f' (x) is a first eye potential signal after the minimum value filtering is applied, n is the number of filter taps which is determined according to the number of taps n outputted from the filtering detail determination unit 110, and i is an integer. Further, min (a, b) is a function that returns the value that is smaller between a and b. Thus, in the minimum value filtering, a sampling value is outputted which has the smallest amplitude in n samples centering on an arbitrary sample f (x) among the eye potential original signals. The first eye potential signal can be obtained by performing the above processing on each of the samples of the eye potential original signals.

Next, processing in the case where the eye potential original signal is inputted into the first path will be described. First, FIG. 4 is a diagram that shows the first eye potential signal obtained by applying the minimum value filtering, by the minimum value filter unit 121, to the eye potential original signal as shown in FIG. 16.

It is to be noted that the unit processing period for the minimum value filtering is set to 0.25 seconds for removing the blink signals from the eye potential original signals. It is to be noted that, the unit processing period indicates a time interval including a sample on which a single minimum value filtering is performed. Further, the number of filter taps n of the minimum value filtering unit 121 is the number of samples included in the unit processing period (0.25 seconds). Thus, the number of filter taps n can be calculated using the unit processing period (0.25 seconds in the above example) and a sampling frequency when A/D conversion is performed on the eye potential original signal.

Figure 4:
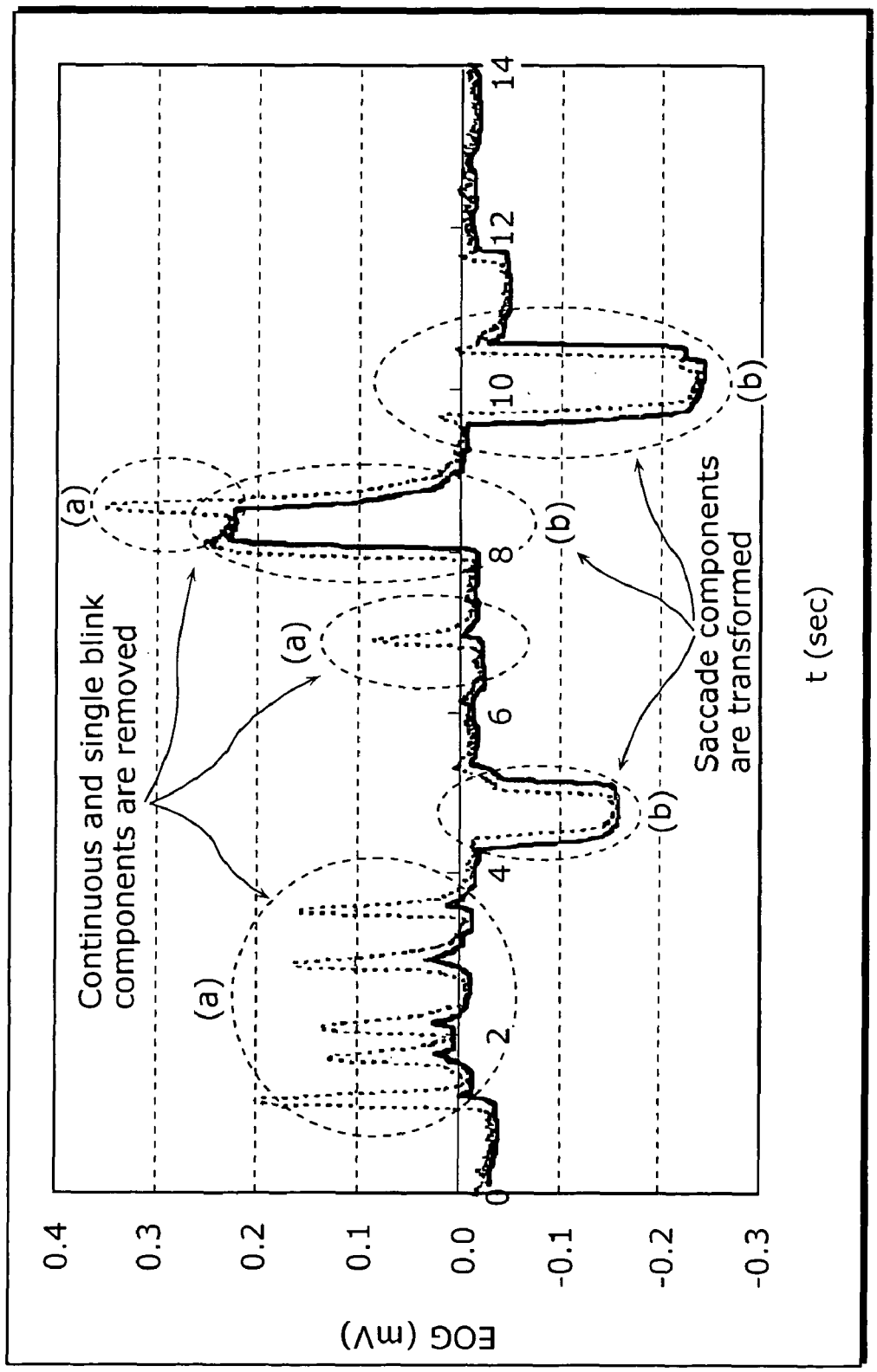
FIG. 4 is a diagram that shows an eye potential signal obtained by applying minimum value filtering to the eye potential signal of FIG. 16.

The regions (a) in FIG. 4 show that consecutive blink signals and an isolated blink signals have been removed by applying the minimum value filtering. However, in the first eye potential signal as shown in FIG. 4, the saccade waveforms have transformed (increased in a temporal width), which is an adverse effect caused by applying the minimum value filtering.

It is to be noted that, although the first embodiment has presented an example where the minimum value filtering is performed by setting the unit processing period of the minimum value filter unit 121 to 0.25 seconds, it can be any value as long as it is longer than a general duration of a single blink=(approximately 0.15 seconds to 0.2 seconds) and shorter than a single fixation time=(approximately 0.3 seconds to 0.4 seconds).

Next, processing of the maximum value filter unit 122 as shown in FIG. 3 will be described.

In the regions (b) as shown in above-mentioned FIG. 4, the temporal widths of the saccade waveforms generated in the negative direction as an adverse effect of the minimum value filtering has increased.

Since the saccade signal is an important signal for tracking a gaze-path, processing is required in which a signal waveform is adjusted to an original temporal width in extracting the generation time.

Thus, the maximum value filter unit 122 applies filtering described below on the first eye potential signal f'(x) outputted from the minimum value filtering unit 121, from which the blink signal has been removed.

$$f''(x)=\max(f''(x), f'(x+i))$$

When n is an odd number, the following applies. $(-n/2 < i < n/2)$

When n is an even number, one of the followings applies. $(-n/2 \leq i < n/2)$ or $(-n/2 < i \leq n/2)$ Here, f" (x) is a second eye potential signal after the maximum value filtering is applied, n is the number of filter taps, and i is an integer. Here, the number of filter taps n corresponds to the number of taps n outputted from the filtering details determination unit 110 and uses the same value as the number of filter taps of the minimum value filtering. Further, max (a, b) is a function that returns the value that is larger between a and b. Thus, in the maximum value filtering, a sampling value is outputted which has the largest amplitude in n samples centering on an arbitrary sample f'(x) among the first eye potential signals. The second eye potential signal can be obtained by performing the above processing on each of the samples of the first eye potential signals.

Figure 5:
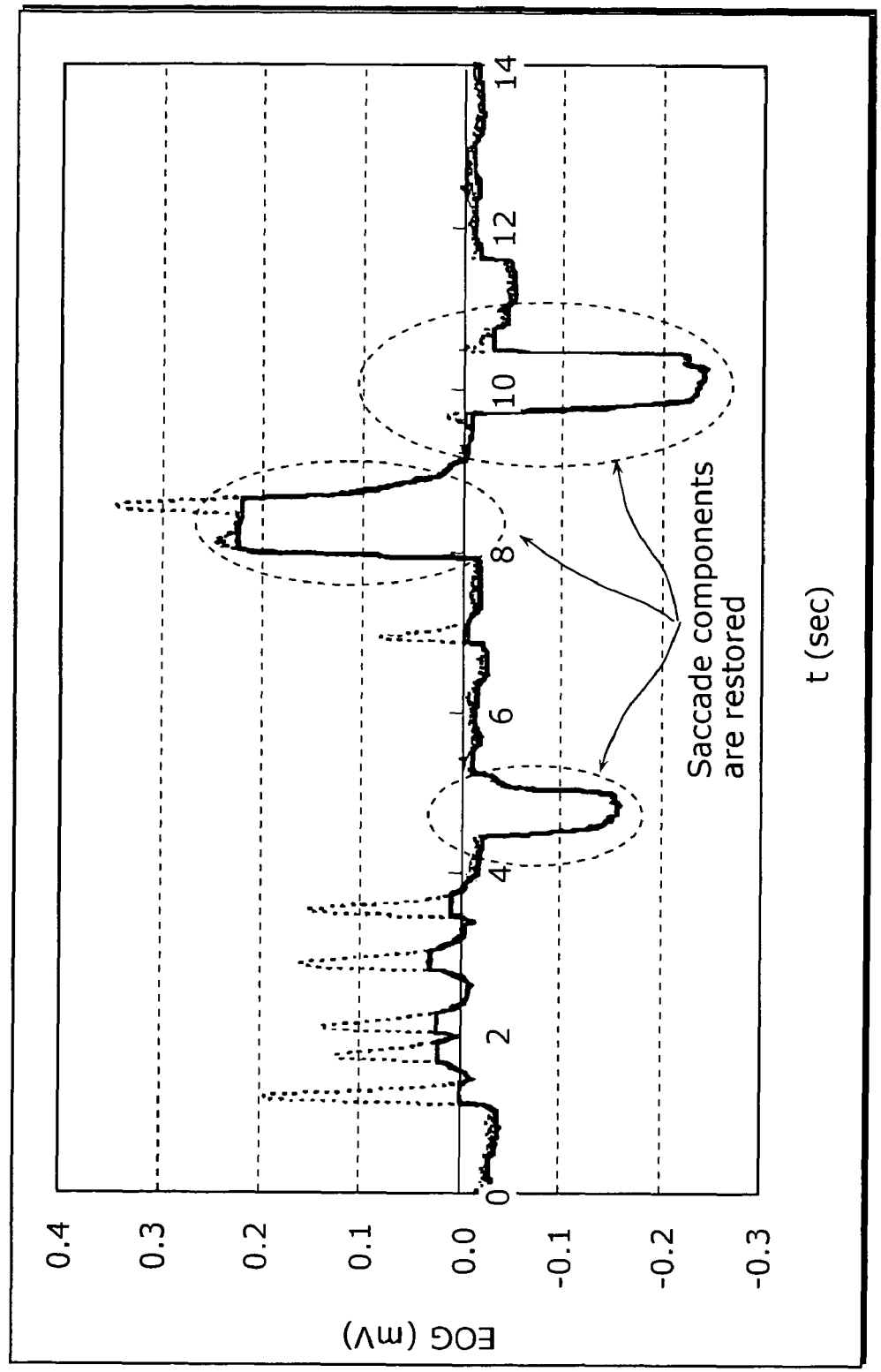
FIG. 5 is a diagram that shows an eye potential signal obtained by applying maximum value filtering to the eye potential signal of FIG. 4.

Next, FIG. 5 is a diagram that shows a second eye potential signal (filtered signal) obtained by applying the maximum value filtering, by the maximum value filter unit 122, to the first eye potential signal as shown in FIG. 4. It is to be noted that, the unit processing period is set to 0.25 seconds as in the case of the minimum value filtering unit 121.

As shown in FIG. 5, the transformed saccade waveform as in FIG. 4 can restore the width of the original signal waveform, by applying the maximum value filtering to the first eye potential signal outputted from the minimum value filter unit 121.

Fundamental processes for the maximum value filter unit 123 and the minimum value filter unit 124 are the same as the maximum value filter unit 122 and the minimum value filter unit 121, respectively, and it is possible to remove the blink signal in the negative direction without affecting the saccade waveform, by performing filtering in order of the maximum value filtering and the minimum value filtering.

It is to be noted that, although the first embodiment has presented an example where the minimum value filtering and the maximum value filtering is employed, a filter that selects a value close to the minimum value or the maximum value may be employed. In this case, it is desirable to select a value approximately 90% of the maximum value or the minimum value.

Further, although the same value is used for the number of filter taps of the minimum value filtering and the maximum value filtering in the first embodiment, a proximate value may be used. In other words, perfect matching is not necessarily required.

In the case where plural filtering processes are applied consecutively, it is sufficient to apply the filtering for removing the effect of the blink signal first, and then apply the filtering for restoring the temporal waveform of saccade.

Further, although the blink signal is removed and the saccade waveform is restored by consecutively applying the minimum value filtering and the maximum value filtering in the first embodiment, only one of the minimum value filtering and the maximum value filtering may be applied without departing from the scope of the present invention when the purpose is only to remove the blink signal.

According to the structure of the above-described first embodiment, the detail of filtering to be performed on an eye potential original signal is determined according to the method of measuring the eye potential original signal, and filtering is performed according to the detail. As a result, it is possible to remove a blink signal properly, even when the electrodes are placed in the opposite orientation, for example.

Further, when the measuring method is such that a blink signal is generated in the positive direction of an eye potential original signal, a filtering detail is determined such that the minimum value filtering and the maximum value filtering are applied consecutively in this order. As a result, it is possible to easily remove a blink signal in the positive direction and restore a saccade waveform.

Further, when the measuring method is such that a blink signal is generated in the negative direction of an eye potential original signal, a filtering detail is determined such that the maximum value filtering and the minimum value filtering are applied consecutively in this order. As a result, it is possible to easily remove a blink signal in the negative direction and restore a saccade waveform.

Second Embodiment

Figure 6:
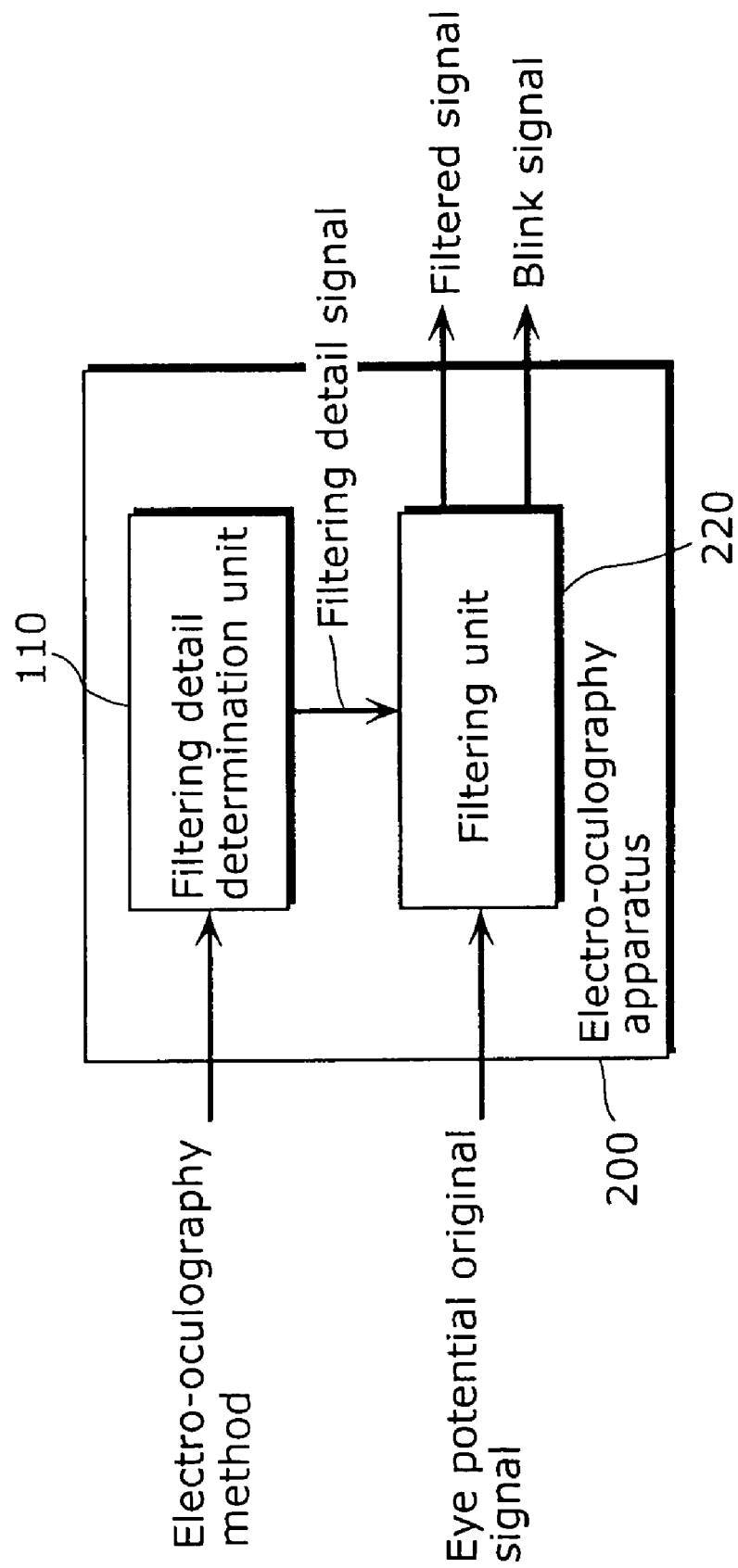
FIG. 6 is a block diagram of an electro-oculography apparatus according to a second embodiment.
Figure 7:
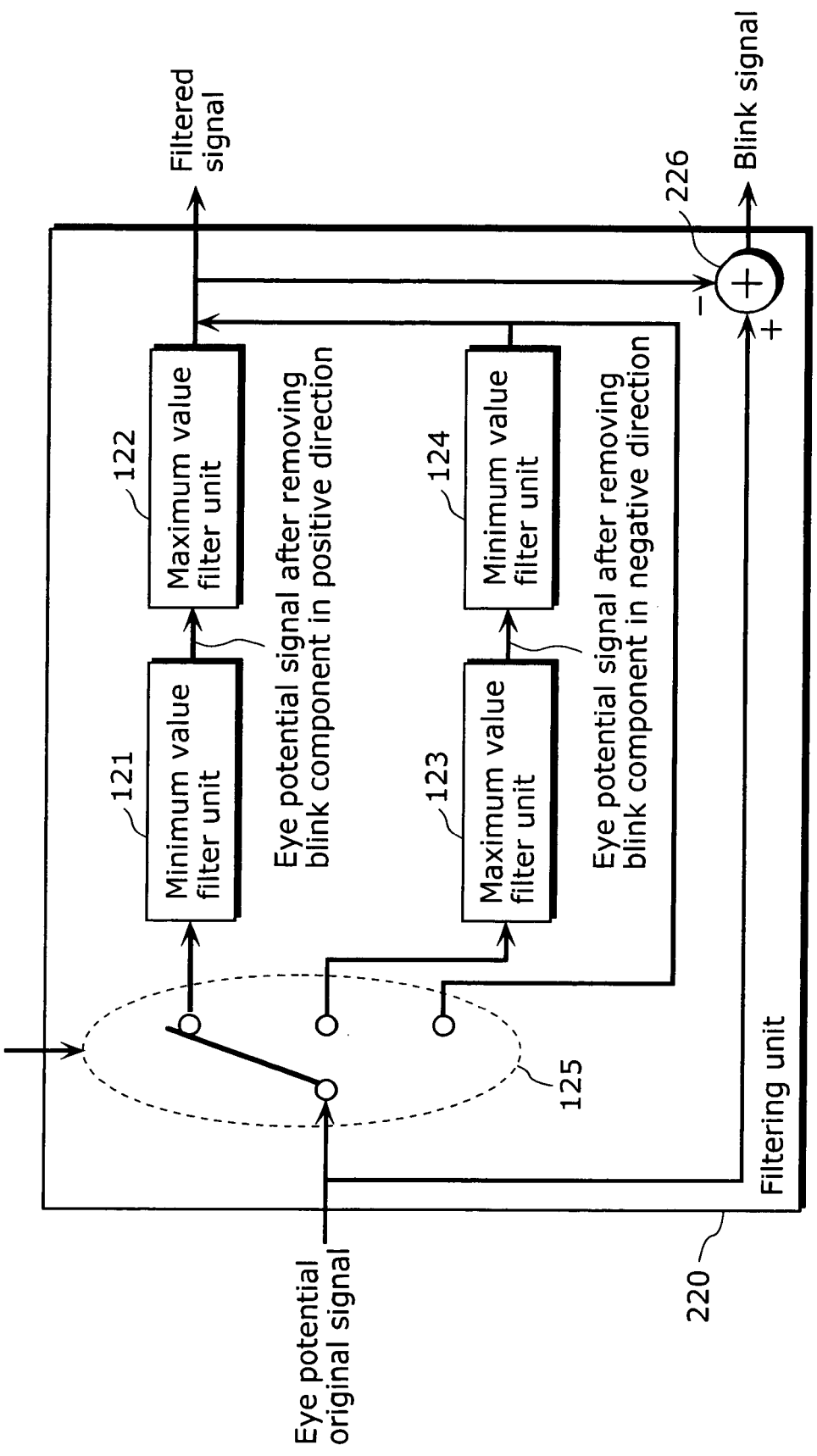
FIG. 7 is a block diagram of a filtering unit as shown in FIG. 6.

FIG. 6 and FIG. 7 are block diagrams of an electro-oculography apparatus 200 according to a second embodiment of the present invention.

The second embodiment differs from the first embodiment in that a filtering unit 220 includes a subtraction unit 226 that subtracts a filtered eye potential signal from the eye potential original signal. The inclusion of the subtraction unit 226 makes it possible to output a blink signal in addition to the filtered signal.

FIG. 7 is a block diagram which shows an example of filtering unit 220 in the electro-oculography apparatus 200 according to the second embodiment. It is to be noted that, since an explanation has already given to the same configuration as FIG. 3, same reference numerical numbers will be given and the explanation will be omitted.

The subtraction unit 226 outputs a difference between the eye potential original signal and the filtered signal. The difference is a blink signal.

Figure 8:
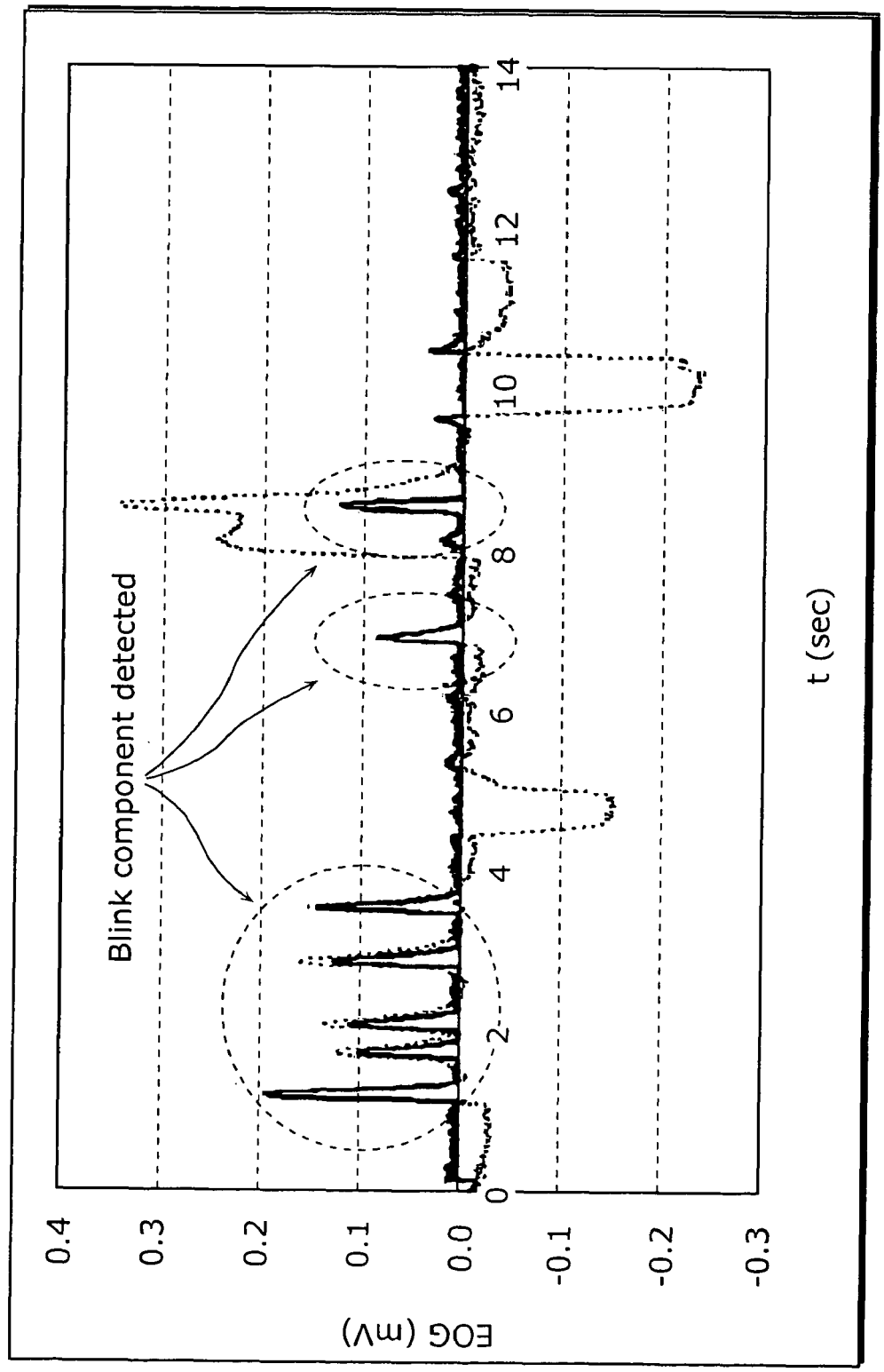
FIG. 8 is a diagram that shows a blink signal obtained by inputting the eye potential signal of FIG. 16 into the filtering unit as shown in FIG. 7.

FIG. 8 shows a blink signal obtained by subtracting the second eye potential signal in FIG. 5 from the eye potential original signal in FIG. 16. It is understood, by referring to FIG. 8, that only the blink signal is detected from the eye potential original signal.

According to the structure of the above-described second embodiment, the detail of filtering to be performed on an eye potential original signal is determined according to the method of measuring the eye potential original signal, and filtering is performed according to the detail. As a result, it is possible to detect a blink signal no matter what a measuring method is employed.

Further, when the measuring method is such that a blink signal is generated in the positive direction of an eye potential original signal, a filtering detail is determined such that the minimum value filtering and the maximum value filtering are applied consecutively in this order. As a result, it is possible to restore a saccade component while easily detecting the blink signal in the positive direction.

Further, when the measuring method is such that a blink signal is generated in the negative direction of an eye potential original signal, a filtering detail is determined such that the maximum value filtering and the minimum value filtering are applied consecutively in this order. As a result, it is possible to restore a saccade component while easily detecting the blink signal in the negative direction.

Third Embodiment

Figure 9:
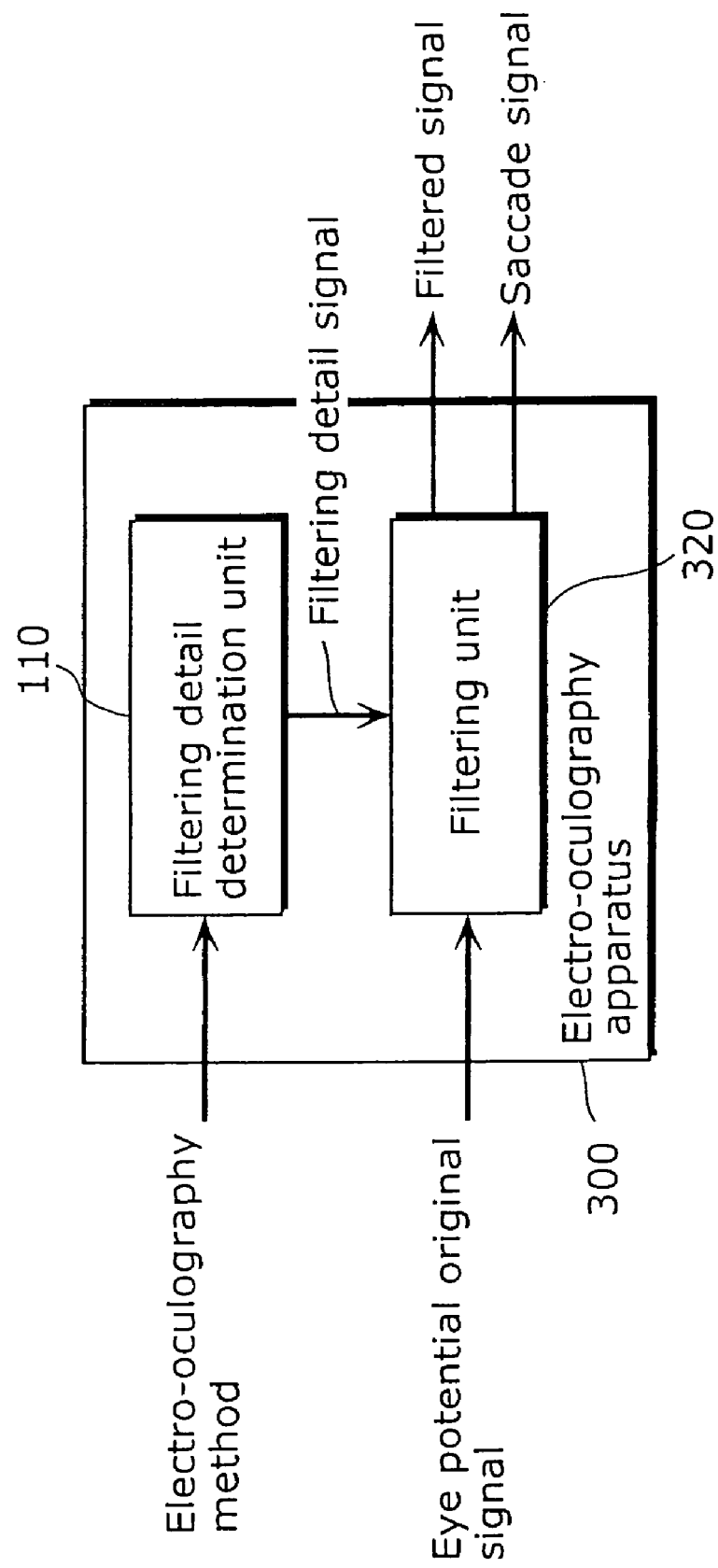
FIG. 9 is a block diagram of an electro-oculography apparatus according to a third embodiment.
Figure 10:
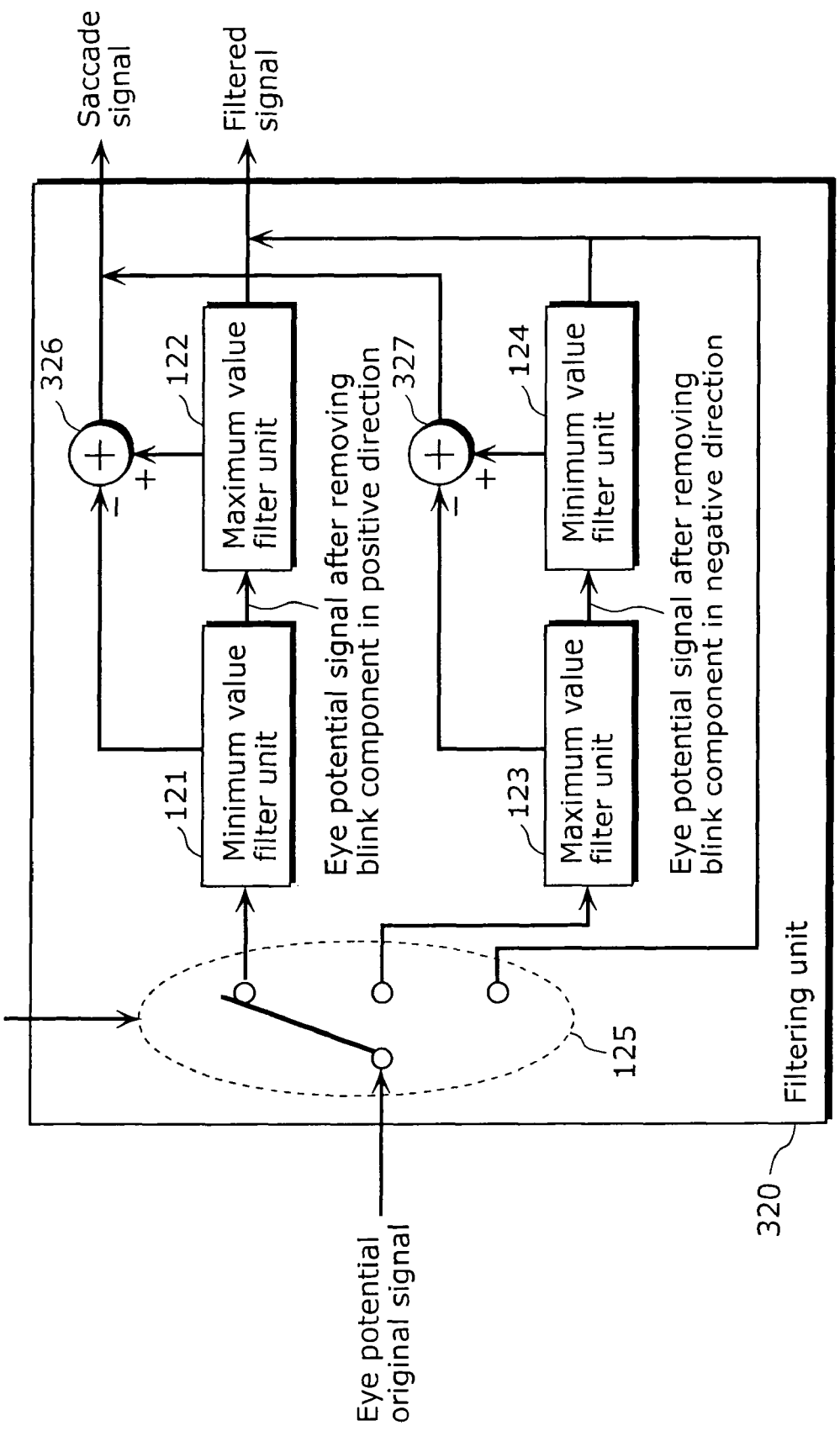
FIG. 10 is a block diagram of a filtering unit as shown in FIG. 9.

FIG. 9 and FIG. 10 are block diagrams of an electro-oculography apparatus 300 according to a third embodiment of the present invention.

The third embodiment differs from the first embodiment in that a filtering unit 320 includes subtraction units 326 and 327 which subtract a signal to which one of the maximum value filtering or the minimum value filtering is applied (a first eye potential signal) from a signal to which both of the maximum value filtering and the minimum value filtering are applied (a second eye potential signal). The inclusion of the subtraction units 326 and 327 makes it possible to output a saccade signal in addition to the filtered signal.

FIG. 10 is a block diagram which shows an example of filtering unit 320 in the electro-oculography apparatus 300 according to the third embodiment. It is to be noted that, since an explanation has already given to the same configuration as FIG. 3, same reference numerical numbers will be given and the explanation will be omitted.

The subtraction unit 326 outputs a saccade signal by subtracting an output signal of the minimum value filter unit 121 from an output signal of the maximum value filter unit 122. Similarly, the subtraction unit 327 outputs a saccade signal by subtracting an output signal of the maximum value filter unit 123 from an output signal of the minimum value filter unit 124.

Figure 11:
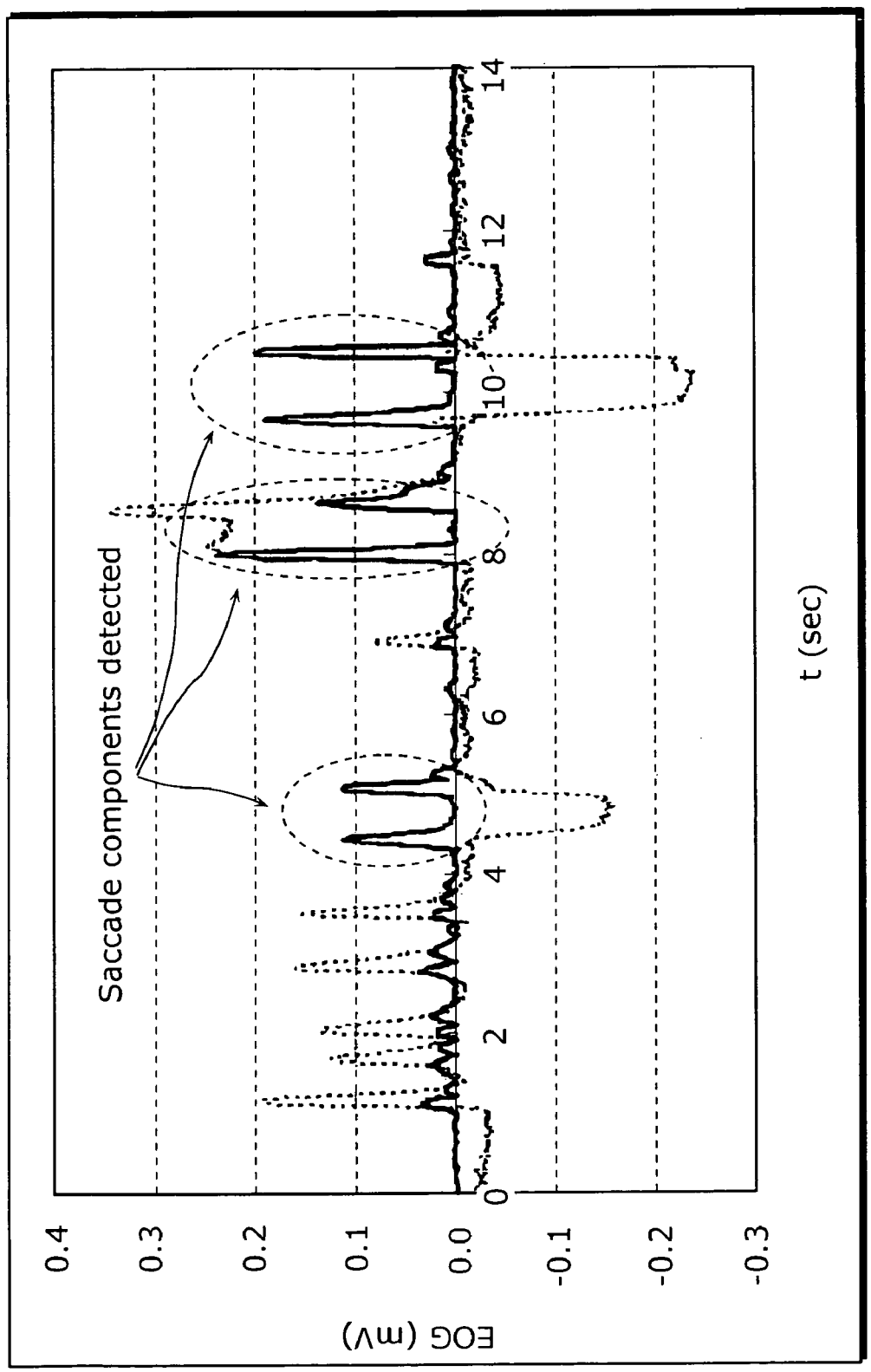
FIG. 11 is a diagram that shows a saccade signal obtained by inputting the eye potential signal of FIG. 16 into the filtering unit as shown in FIG. 10.

FIG. 11 shows a saccade signal obtained by subtracting the first eye potential signal in FIG. 4, to which the minimum value filtering has been applied, from the second eye potential signal in FIG. 5, to which the maximum value filtering has been applied. It is understood, by referring to FIG. 11, that only the saccade signal is detected from the eye potential original signal.

According to the structure of the above-described third embodiment, the detail of filtering to be performed on an eye potential original signal is determined according to the method of measuring the eye potential original signal, and filtering is performed according to the detail. As a result, it is possible to detect a saccade signal no matter what a measuring method is employed.

Further, when the measuring method is such that a blink signal is generated in the positive direction of an eye potential original signal, a filtering detail is determined such that the minimum value filtering and the maximum value filtering are applied consecutively in this order, and further that the first eye potential signal to which the minimum value filtering is applied is subtracted from the second eye potential signal to which the maximum value filtering is applied. As a result, it produces an advantageous effect that the saccade signal can be detected while removing the blink signal of the positive direction.

Further, in the third embodiment, there is an advantageous effect that it is possible to detect a saccade signal including a generation time of the saccade signal by setting the number of filter taps of the maximum value filtering as greater than the number of filter taps of the minimum value filtering.

On the other hand, when the measuring method is such that a blink signal is generated in the negative direction of an eye potential original signal, a filtering detail is determined such that the maximum value filtering and the minimum value filtering are applied consecutively in this order, and further that the first eye potential signal to which the maximum value filtering is applied is subtracted from the second eye potential signal to which minimum value filtering is applied. As a result, it produces an advantageous effect that the saccade signal can be detected while removing the blink signal in the negative direction. In this case, the saccade signal appears invariably in the negative direction (the waveform is reversed from the one in FIG. 11). Therefore, it is necessary to add a process to invert positive and negative in order to obtain a signal as shown in FIG. 11. On the other hand, in the case where the saccade signal is used only for detecting a generation timing of the saccade, there is no need to invert positive and negative.

Further, in the third embodiment, there is an advantageous effect that it is possible to detect a saccade signal including a generation time of the saccade signal by setting the number of filter taps of the minimum value filtering as greater than the number of filter taps of the maximum value filtering.

It is to be noted that, removing a blink signal, detecting a blink signal, or detecting a saccade signal has been focused in each of the above-described embodiments, and the number of the filter taps of filtering to be applied first between the minimum value filtering and the maximum value filtering has been described. The number of the filter taps may be used for removing a muscle potential, a noise, and the like, by being adjusted to the muscle potential, the noise, and the like.

Fourth Embodiment

Figure 12:
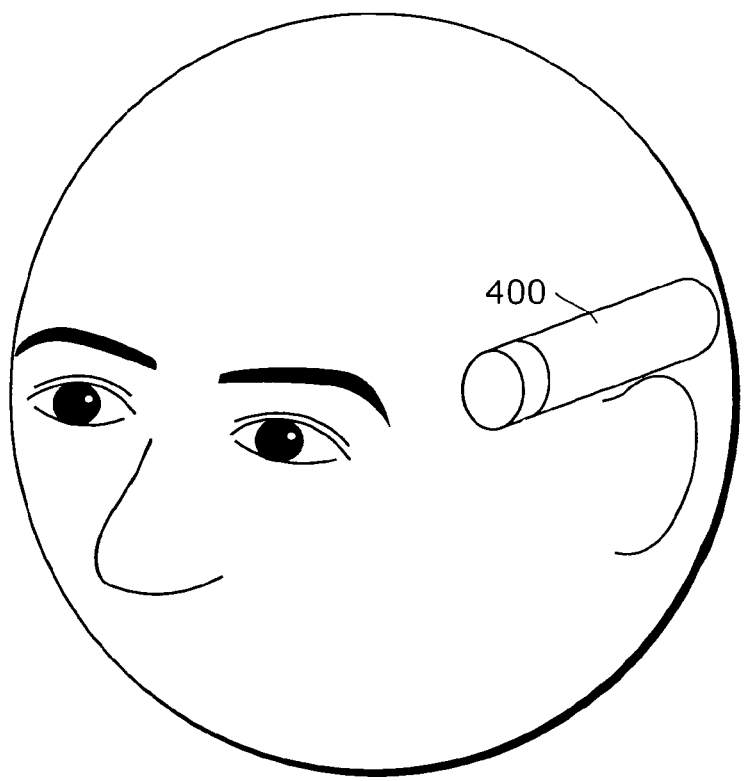
FIG. 12 is a diagram that shows an imaging apparatus worn by a user according to a fourth embodiment.
Figure 13:
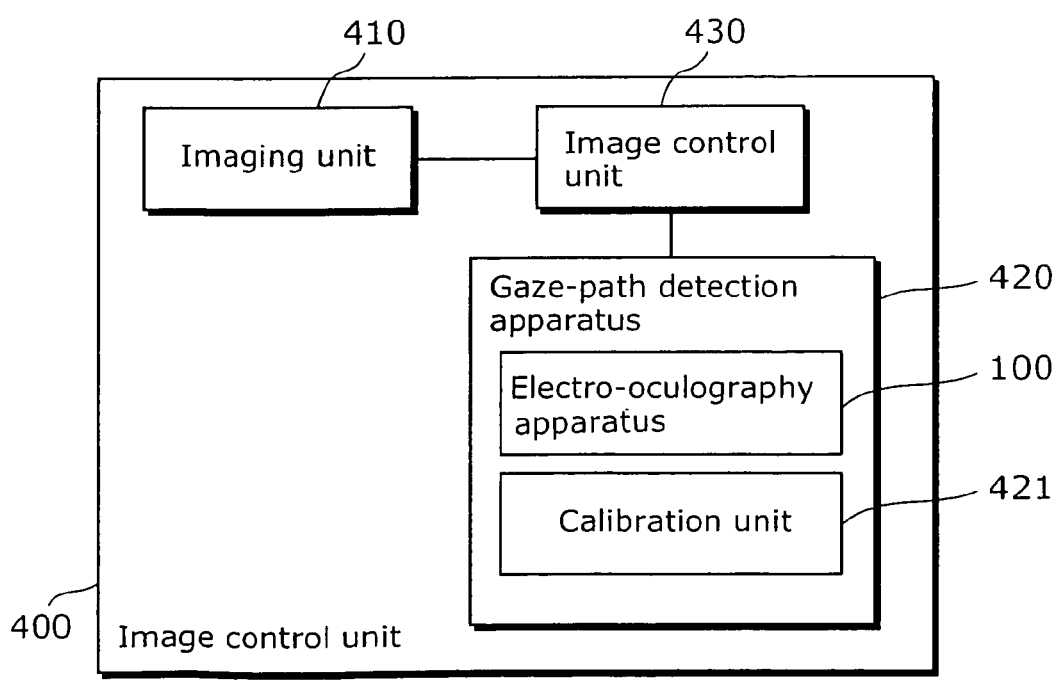
FIG. 13 is a block diagram of the imaging apparatus according to the fourth embodiment.

FIG. 12 and FIG. 13 are block diagrams of an imaging apparatus 400 according to a fourth embodiment of the present invention. The imaging apparatus 400 is worn by a user on a temporal part, and images gaze direction of the user. More specifically, the imaging apparatus 400 includes an imaging unit 410, a gaze-path detection apparatus 420, and an image control unit 430.

The imaging unit 410 may be a camera that takes a still picture, or may be a video camera the shoots a moving image, for example. The gaze-path detection apparatus 420 includes, for example, the electro-oculography apparatus 100 according to the first embodiment, and a calibration unit 421 that calibrates an output signal of the eye potential measure apparatus 100 (filtered signal) to a gaze-point (gaze direction) of the user.

The electro-oculography apparatus 100 obtains an eye potential original signal from, for example, electrodes placed above and below the left temple of the user as shown in FIG. 12. Then, the electro-oculography apparatus 100 outputs a filtered signal of which a blink signal is removed through one of the first to third paths in FIG. 3.

The calibration unit 421 calculates a gaze-point of a subject user from the filtered signal by using a calibration parameter held in advance. It is to be noted that a method of detecting the gaze-point is not specifically defined, and may include calculating a moved angle of an eyeball using a filtered signal.

In this case, the calibration parameter is a parameter for converting the filtered signal into a moved angle of an eyeball and includes a calibration coefficient α used in an expression 1 indicated below. It is generally known that a measured eye potential $V_{a-b}$ changes linearly when the moved angle of an eyeball θ is within a fixed range. Therefore, the measured eye potential $V_{a-b}$ can be approximated by the expression below using the calibration coefficient α and the moved angle of an eyeball θ.

[Expression 1]

$$V_{a-b} = \alpha \times \theta \quad \text{(expression 1)}$$

Then, the image control unit 430 monitors an output signal from the gaze-path detection apparatus 420 and change an orientation of the imaging unit 410 following a movement of gaze-path of a user. This allows the imaging unit 410 to take an image of the gaze direction of the user. Since the blink signal has been removed from the signal outputted from the electro-oculography apparatus 100, the calibration unit 421 can accurately identify the gaze-position of the user. As a result, it is possible to take an image of a gaze direction of the user accurately while eliminating an effect of a blink.

However, the gaze-path detection apparatus 420 according to the fourth embodiment is not limited to the above application. Other applications include an application into an apparatus that plots a gaze-point of a user detected by the gaze-path detection apparatus 420 on an image captured by the imaging apparatus. Further, the same advantageous effect can be obtained by mounting on the electro-oculography apparatuses 200 or 300 according to the second and third embodiment, respectively, instead of the electro-oculography apparatus 100 according to the first embodiment.

(Other Modifications)

It is to be Noted that, Although the Present Invention has been described according to each of the first to third embodiments described above, the present invention is not limited to each of the first to fourth embodiments described above. The present invention includes cases below.

(1) Each device mentioned above is, to be specific, a computer system that includes a microprocessor, a ROM, a RAM, a hard disk unit, a display unit, a keyboard, a mouse, and so on. A computer program is stored on the RAM or the hard disk unit. The microprocessor operates according to the computer program, so that each device achieves its function. Here, the computer program is configured by combining plural instruction codes indicating instructions for a computer in order to implement a predetermined function.

(2) A part or all of the constituent elements constituting the respective apparatuses may be configured from a single System-LSI (Large-Scale Integration). The System-LSI is a super-multi-function LSI manufactured by integrating constituent units on one chip, and is specifically a computer system configured by including a microprocessor, a ROM, a RAM, and so on. A computer program is stored in the RAM. The System-LSI achieves its function through the microprocessor's operation according to the computer program.

(3) A part or all of the constituent elements included in the respective apparatuses may be configured as an IC card which can be attached and detached from the respective apparatuses or as a stand-alone module. The IC card or the module is a computer system configured from a microprocessor, a ROM, a RAM, and the so on. The IC card or the module may also include the aforementioned super-multi-function LSI. The IC card or the module achieves its function through the microprocessor's operation according to the computer program. The IC card or the module may also be implemented to be tamper-resistant.

(4) The present invention may be a method as described above. Further, the present invention may be a computer program for realizing the above-described method using a computer, and may also be a digital signal including the computer program.

Furthermore, the present invention may also be realized by storing the computer program or the digital signal in a computer readable recording medium such as flexible disc, a hard disk, a CD-ROM, an MO, a DVD, a DVD-ROM, a DVD-RAM, a BD (Blu-ray Disc), and a semiconductor memory. Furthermore, the present invention also includes the digital signal recorded in these recording media.

Furthermore, the present invention may also be realized by the transmission of the aforementioned computer program or digital signal via a telecommunication line, a wireless or wired communication line, a network represented by the Internet, a data broadcast and so on.

The present invention may also be a computer system including a microprocessor and a memory, in which the memory stores the aforementioned computer program and the microprocessor operates according to the computer program.

Furthermore, by transferring the program or the digital signal by recording onto the aforementioned recording media, or by transferring the program or digital signal via the aforementioned network and the like, execution using another independent computer system is also made possible.

(5) Each of the above-mentioned embodiments may be applied to each of the above-described modification examples.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

INDUSTRIAL APPLICABILITY

The present invention is useful as a device and the like which record and reproduce an image or a voice in areas including broadcasting, communication, and storage. Further, the present invention can also be implemented as a still picture record and reproduction device and so on. Furthermore, the present invention can also be implemented as a health and medical device.

What is claimed is:

1. An electro-oculography apparatus that measures an eye potential of a user, said electro-oculography apparatus comprising:
an eye potential measuring unit configured to measure the eye potential generated by an eye movement of the user and to output an eye potential original signal based on the measured eye potential;
a first filtering unit configured to receive the eye potential original signal output from said eye potential measuring unit and to output a first eye potential signal by applying one of a maximum value filtering and a minimum value filtering to the received eye potential original signal;
a second filtering unit configured to receive the first eye potential signal output from said first filtering unit and to output a second eye potential signal by applying the other of the maximum value filtering and the minimum value filtering to the received first eye potential signal; and
a filtering detail determination unit configured to determine the filtering to be performed by said first filtering unit and said second filtering unit, based on a blink signal included in the eye potential original signal, the blink signal being generated when the user blinks,
wherein, for a signal comprising a plurality of samples, the maximum value filtering replaces a value of each respective sample with a sample value having a largest amplitude from among a plurality of samples centering on the respective sample,
wherein, for a signal comprising a plurality of samples, the minimum value filtering replaces a value of each respective sample with a sample value having a smallest amplitude from among a plurality of samples centering on the respective sample, and wherein, when the blink signal has a positive potential, said filtering detail determination unit causes said first filtering unit to perform the minimum value filtering to the received eye potential original signal and causes said second filtering unit to perform the maximum value filtering to the received first eye potential signal.

2. The electro-oculography apparatus according to claim 1, wherein the minimum value filtering has a unit processing period that is equal to a unit processing period of the maximum value filtering.

3. The electro-oculography apparatus according to claim 1, further comprising a subtraction unit subtracting the second eye potential signal from the eye potential original signal.

4. The electro-oculography apparatus according to claim 1, further comprising a subtraction unit subtracting the first eye potential signal from the second eye potential signal.

5. The electro-oculography apparatus according to claim 1, wherein a unit processing period of each of the maximum value filtering and the minimum value filtering is equal to or greater than a blink duration of the user and less than a fixation time.

6. The electro-oculography apparatus according to claim 1, wherein, when the blink signal has a negative potential, said filtering detail determination unit causes said first filtering unit to perform the maximum value filtering to the received eye potential original signal, and causes said second filtering unit to perform the minimum value filtering to the received first eye signal.

7. An imaging apparatus that images a gaze direction of the user, said imaging apparatus comprising:
   an imaging unit;
   said electro-oculography apparatus of claim 1;
   a calibration unit configured to detect the gaze direction of the user, using an output signal of said electro-oculography apparatus; and
   an image control unit configured to cause said imaging unit to image the gaze direction detected by said calibration unit.

8. An electro-oculography method for measuring an eye potential of a user, said electro-oculography method comprising:
   measuring the eye potential generated by an eye movement of the user and outputting an eye potential original signal based on the measured eye potential;
   receiving the eye potential signal and outputting a first eye potential signal by applying one of a maximum value filtering and a minimum value filtering to the received eye potential original signal;
   receiving the output first eye potential signal and outputting a second eye potential signal by applying the other of the maximum value filtering and the minimum value filtering to the received first eye potential signal; and
   determining the filtering to be performed by said outputting of the first eye potential signal and said outputting of the second eye potential signal, based on a blink signal included in the eye potential original signal, the blink signal being generated when the user blinks,
   wherein, for a signal comprising a plurality of samples, the maximum value filtering replaces a value of each respective sample with a sample value having a largest amplitude from among a plurality of samples centering on the respective sample,
   wherein, for a signal comprising a plurality of samples, the minimum value filtering replaces a value of each respective sample with a sample value having a smallest amplitude from among a plurality of samples centering on the respective sample, and
   wherein, when the blink signal has a positive potential, said determining of the filtering causes said outputting of the first eye potential signal to perform the minimum value filtering to the received eye potential original signal and causes said outputting of the second eye potential signal to perform the maximum value filtering to the received first eye potential signal.

9. A non-transitory computer-readable recording medium having a computer program recorded thereon, the program for measuring an eye potential of a user, and the program causing a computer to execute a method comprising:
   measuring the eye potential generated by an eye movement of the user and outputting an eye potential original signal based on the measured eye potential;
   receiving the eye potential signal and outputting a first eye potential signal by applying one of a maximum value filtering and a minimum value filtering to the received eye potential original signal;
   receiving the output first eye potential signal and outputting a second eye potential signal by applying the other of the maximum value filtering and the minimum value filtering to the received first eye potential signal; and
   determining the filtering to be performed by said outputting of the first eye potential signal and said outputting of the second eye potential signal, based on a blink signal included in the eye potential original signal, the blink signal being generated when the user blinks,
   wherein, for a signal comprising a plurality of samples, the maximum value filtering replaces a value of each respective sample with a sample value having a largest amplitude from among a plurality of samples centering on the respective sample,
   wherein, for a signal comprising a plurality of samples, the minimum value filtering replaces a value of each respective sample with a sample value having a smallest amplitude from among a plurality of samples centering on the respective sample, and
   wherein, when the blink signal has a positive potential, said determining of the filtering causes said outputting of the first eye potential signal to perform the minimum value filtering to the received eye potential original signal and causes said outputting of the second eye potential signal to perform the maximum value filtering to the received first eye potential signal.

10. An integrated circuit that measures an eye potential of a user when connected to an eye potential measuring unit that measures an eye potential generated by an eye movement of the user and outputs an eye potential original signal based on the measured eye potential, said integrated circuit comprising:
   a first filtering unit configured to receive the eye potential original signal output from the eye potential measuring unit and to output a first eye potential signal by applying one of a maximum value filtering and a minimum value filtering to the received eye potential original signal;
   a second filtering unit configured to receive the first eye potential signal output from said first filtering unit and to output a second eye potential signal by applying the other of the maximum value filtering and the minimum value filtering to the received first eye potential signal; and
   a filtering detail determination unit configured to determine the filtering to be performed by said first filtering unit and said second filtering unit, based on a blink signal included in the eye potential original signal, the blink signal being generated when the user blinks, wherein, for a signal comprising a plurality of samples, the maximum value filtering replaces a value of each respective sample with a sample value having a largest amplitude from among a plurality of samples centering on the respective sample, wherein, for a signal comprising a plurality of samples, the minimum value filtering replaces a value of each respective sample with a sample value having a smallest amplitude from among a plurality of samples centering on the respective sample, and wherein, when the blink signal has a positive potential, said filtering detail determination unit causes said first filtering unit to perform the minimum value filtering to the received eye potential original signal and causes said second filtering unit to perform the maximum value filtering to the received first eye potential signal.

* * * * *